(12) United States Patent
Bateman et al.

(10) Patent No.: US 10,603,454 B2
(45) Date of Patent: Mar. 31, 2020

(54) TRACHEOSTOMY TUBE ASSEMBLIES AND INNER CANNULAE

(71) Applicant: SMITHS MEDICAL INTERNATIONAL LIMITED, Ashford (GB)

(72) Inventors: Timothy Bateman, Hythe (GB); Steven James Field, Canterbury (GB); Andrew Thomas Jeffrey, Hythe (GB); Neil Steven Veasey, Ashford (GB); Christopher John Woosnam, Great Sutton (GB)

(73) Assignee: SMITHS MEDICAL INTERNATIONAL LIMITED, Ashford, Kent (GB)

( * ) Notice: Subject to any disclaimer, the term of this patent is extended or adjusted under 35 U.S.C. 154(b) by 326 days.

(21) Appl. No.: 15/565,085

(22) PCT Filed: Apr. 2, 2016

(86) PCT No.: PCT/GB2016/000069
§ 371 (c)(1),
(2) Date: Oct. 6, 2017

(87) PCT Pub. No.: WO2016/166498
PCT Pub. Date: Oct. 20, 2016

(65) Prior Publication Data
US 2018/0104428 A1    Apr. 19, 2018

(30) Foreign Application Priority Data

Apr. 16, 2015    (GB) .................................. 1506545.1

(51) Int. Cl.
*A61M 16/04* (2006.01)
*A61M 16/08* (2006.01)
*A61M 25/00* (2006.01)

(52) U.S. Cl.
CPC ........ *A61M 16/0427* (2014.02); *A61M 16/04* (2013.01); *A61M 16/045* (2014.02);
(Continued)

(58) Field of Classification Search
CPC .............. A61M 16/04; A61M 16/0427; A61M 16/0429; A61M 16/0434; A61M 16/045;
(Continued)

(56) References Cited

U.S. PATENT DOCUMENTS 6,135,110 A  * 10/2000 Roy .................. A61M 16/0465
128/207.14
2009/0064999 A1* 3/2009 Marten ............. A61M 16/0465
128/200.26

(Continued)

FOREIGN PATENT DOCUMENTS

DE           19707364 C1    12/1997

OTHER PUBLICATIONS

PCT International Search Report and Written Opinion, PCT/GB2016/000069, EPO dated Jun. 17, 2016.

*Primary Examiner* — Joseph D. Boecker
(74) *Attorney, Agent, or Firm* — Louis Woo

(57) ABSTRACT

A tracheostomy tube assembly comprises an outer tracheostomy tube (1) and an inner cannula (20) fitted in the tube. The machine end of the inner cannula has a collapsible region (22) formed by a plurality of curved or bent struts (26) extending parallel with one another between a machine end collar (28) and a patient end collar (27). The struts (26) carry outwardly-projecting catches (23) arranged to engage a rib (24) extending around the inside of a hub (16) at the machine end of the tube and thereby resist removal of the cannula from the tube. The inner cannula (20) is removed by twisting the machine end collar (28) so that the struts (26) collapse inwardly and thereby disengage the catches (23) from the rib (24).

9 Claims, 5 Drawing Sheets

(52) U.S. Cl.
CPC ..... *A61M 16/0465* (2013.01); *A61M 16/0816* (2013.01); *A61M 2025/0006* (2013.01)

(58) Field of Classification Search
CPC .......... A61M 16/0465; A61M 16/0472; A61M 16/0488; A61M 16/0497; A61M 2025/0006; A61M 2025/0175; A61M 2025/0681; Y10S 128/912
See application file for complete search history.

(56) References Cited

U.S. PATENT DOCUMENTS

| | | | |
|---|---|---|---|
| 2010/0244432 A1 | 9/2010 | Neame et al. | |
| 2011/0083672 A1* | 4/2011 | Webster | A61M 16/0465 128/207.15 |
| 2013/0269704 A1* | 10/2013 | Thomas | A61M 16/04 128/207.29 |
| 2014/0034048 A1* | 2/2014 | Bruggeman | A61M 16/0465 128/200.26 |
| 2014/0238389 A1* | 8/2014 | Bruggemann | A61M 16/0427 128/200.26 |
| 2015/0136123 A1* | 5/2015 | Donlon | A61M 16/0497 128/200.26 |
| 2018/0133423 A1* | 5/2018 | Bateman | A61M 16/0465 |
| 2018/0169362 A1* | 6/2018 | Bateman | A61M 16/0465 |

\* cited by examiner

TRACHEOSTOMY TUBE ASSEMBLIES AND INNER CANNULAE

This invention relates to inner cannulae of the kind for a tracheostomy tube, the inner cannula including a tubular shaft and a machine end region arranged to fit within a hub at the machine end of the tracheostomy tube.

Tracheostomy tube assemblies commonly include an outer tube and an inner tube or cannula that is a removable fit within the outer tube. The inner cannula can be removed and replaced periodically to ensure that the passage through the assembly does not become blocked by secretions. This avoids the need to remove the outer tube frequently.

The inner cannula presents various problems because it must be thin walled and a close fit within the outer tube so as to provide a large bore and thereby limit the resistance to flow of gas along the assembly. It must, however, also be sufficiently stiff to be inserted in the outer tube without buckling or kinking and must be readily removable, preferably with only minimal force being exerted on the tube. WO94/01156 and WO2004/101048 describe inner cannulae made of PTFE. EP1938857 describes an arrangement of tracheostomy tubes and inner cannulae where the hubs of the inner cannulae of different sizes are shaped differently so that they will only fit in the appropriate tracheostomy tube. EP2224985 describes an arrangement for attaching a hub to the shaft of an inner cannula. GB2056285 describes an inner cannula having a wall corrugated both externally and internally and a longitudinal groove or other reinforcement member traversing at least some of the corrugations. U.S. Pat. No. 4,817,598 describes a smooth-walled inner cannula having a ring-pull formation at its rear, machine end. U.S. Pat. No. 5,119,811 describes an inner cannula with a flared patient end and formed of two layers of different materials. U.S. Pat. No. 5,386,826 describes an inner cannula with an outer helical filament or layer of low friction material. U.S. Pat. No. 5,983,895 describes an inner cannula with straight sections at opposite ends joined by an intermediate curved section. U.S. Pat. No. 6,019,753 describes an inner cannula with two elongate regions of different flexibility so that the cannula has a plane of preferential bending. U.S. Pat. No. 6,019,753 describes an inner cannula having a shaft formed with slots to make it more flexible, the slots being covered by an outer thin sheath. U.S. Pat. No. 6,135,110 describes a curved inner cannula that is retained with the outer tube by means of a rotatable spring fitting.

It is an object of the present invention to provide an alternative inner cannula and tracheostomy tube assembly.

According to one aspect of the present invention there is provided an inner cannula of the above-specified kind, characterised in that the outer surface of the machine end region of the inner cannula and the inner surface of the hub on the tracheostomy tube are provided with cooperating engagement formations arranged to retain the inner cannula in the hub of the tracheostomy tube against an axial force tending to withdraw the inner cannula from the tracheostomy tube, and that the machine end region is arranged such that twisting an outer end of the machine end region about the axis of the inner cannula displaces the engagement formation on the inner cannula away from the engagement formation on the hub sufficiently to allow the inner cannula to be pulled rearwardly out of the tracheostomy tube.

The outer end of the machine end region may connect with its forward end by a collapsible region, the or each engagement formation on the machine end region being provided on the collapsible region such that twisting the outer end of the machine end region relative to the forward end causes the collapsible region to collapse inwardly and displace the or each engagement formation on the machine end region inwardly out of engagement with the or each engagement formation on the hub. The collapsible region may be provided by a plurality of struts extending generally parallel to one another and extending generally longitudinally of the machine end region. The struts are preferably curved or bent along their length. The struts may extend forwardly from a circular machine end collar, and the collar may be formed with a plurality of grooves around its inner surface to enable the collar to buckle when twisted. The inner cannula may include a machine end grip having two hinged rings mounted with the machine end of the inner cannula such that the rings can be folded together and gripped to enable the machine end of the inner cannula to be twisted and pulled rearwardly. The or each engagement formation on the hub and end region may extend around only a part of the circumference of the hub and end region such that the engagement formations on the hub and end region can be displaced out of engagement by twisting the machine end region relative to the hub to enable the inner cannula to be removed from the tracheostomy tube. The inner cannula may have at least a part of its length that is flexible about its axis such that the machine end of the inner cannula can be angularly displaced relative to the patient end of the inner cannula. Alternatively, the inner cannula may have a separate rotatable component, the engagement formations on the inner cannula being provided on the rotatable component.

According to another aspect of the present invention there is provided a tracheostomy tube assembly including a tracheostomy tube and an inner cannula according to the above one aspect of the invention fitted in the tube.

An inner cannula and a tracheostomy tube assembly including an inner cannula both in accordance with the present invention, will now be described, by way of example, with reference to the accompanying drawings, which are not to scale, and in which.

Figure 1:
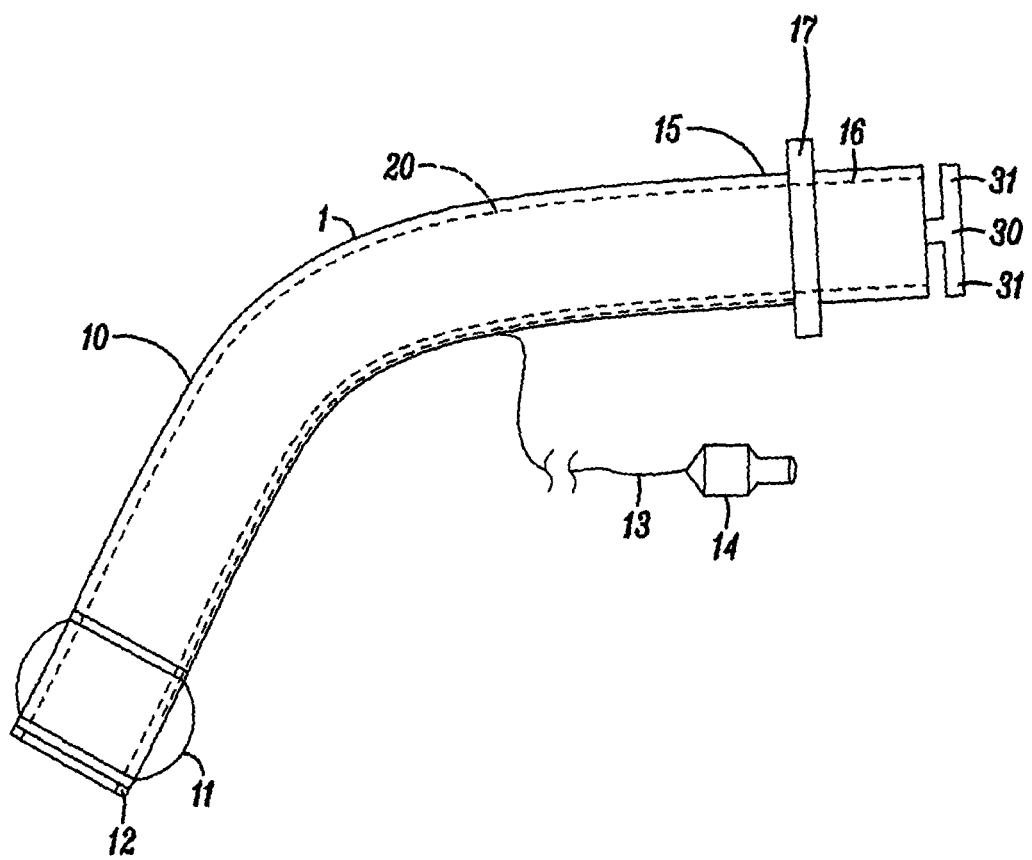
FIG. 1 is a side elevation view of a tracheostomy tube assembly including an inner cannula.
Figure 2:
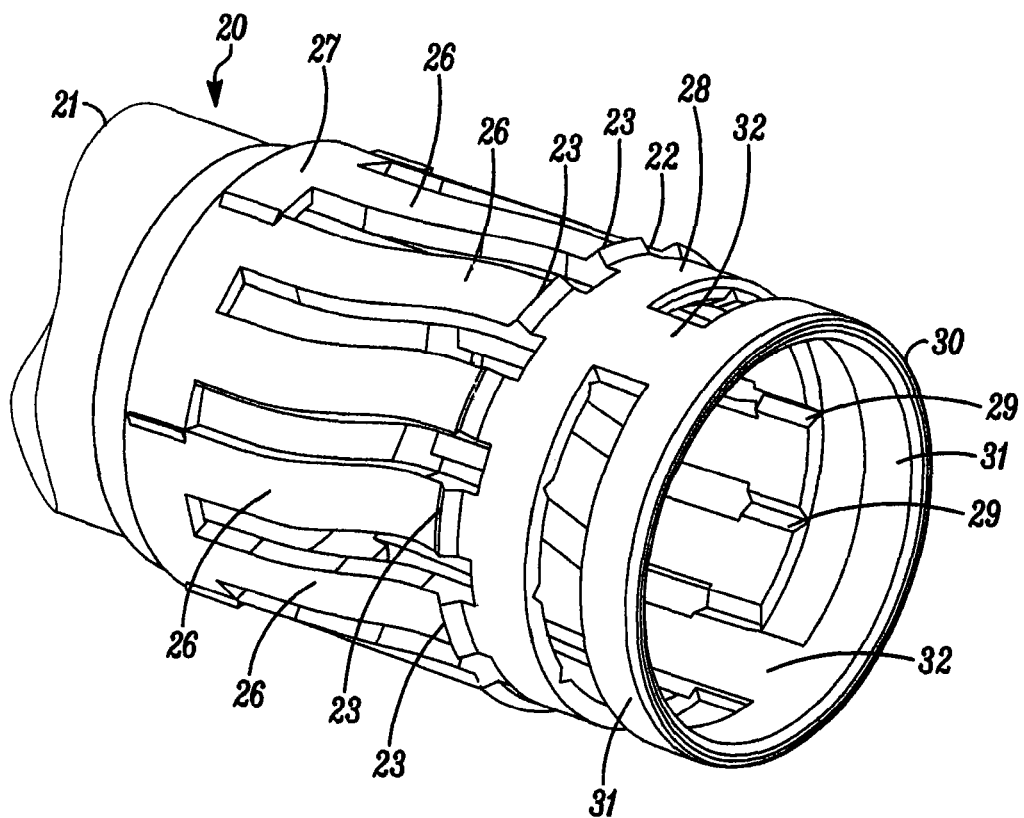
FIG. 2 is an enlarged perspective view of the machine end of a first form of inner cannula.
Figure 3:
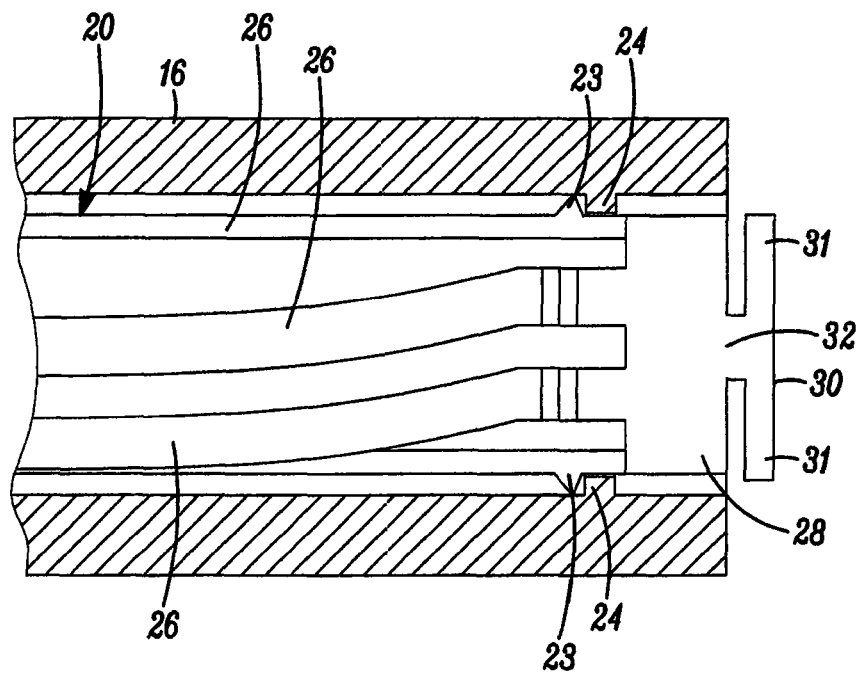
FIG. 3 is a cross-sectional, side elevation view of the machine end of the inner cannula engaged within the hub of the tracheostomy tube.
Figure 4:
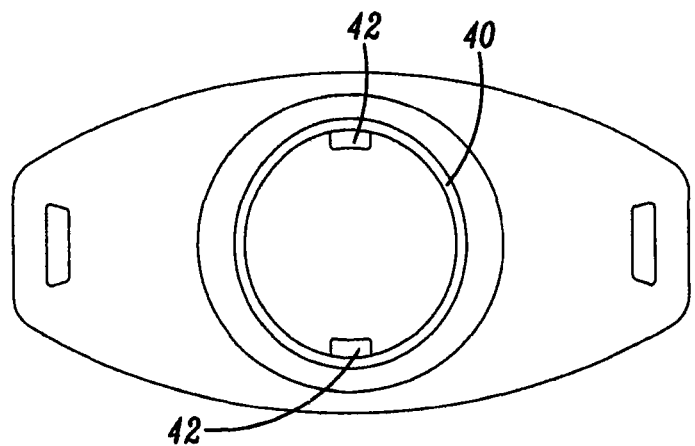
FIG. 4 is an end view of the machine end of a tracheostomy tube for an alternative, second assembly.
Figure 5:
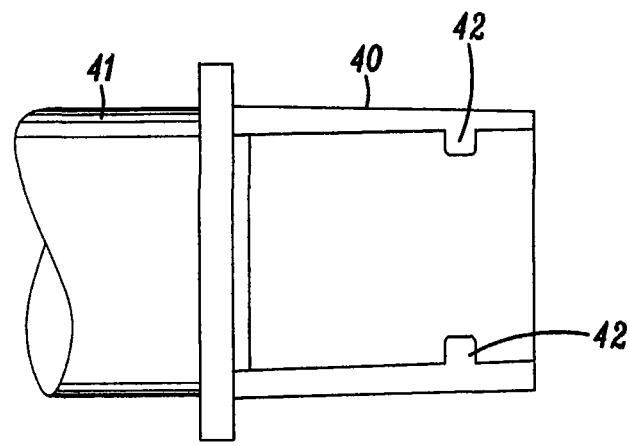
FIG. 5 is a cross-sectional side elevation view of the machine end hub of the second form of tube in FIG. 4.
Figure 6:
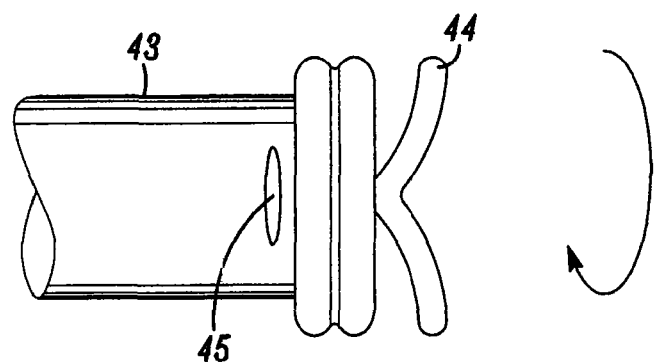
FIGS. 6 and 7 are side elevation views of the machine end of an inner cannula for the second form of tube shown in FIGS. 4 and 5 along orthogonal axes.
Figure 7:
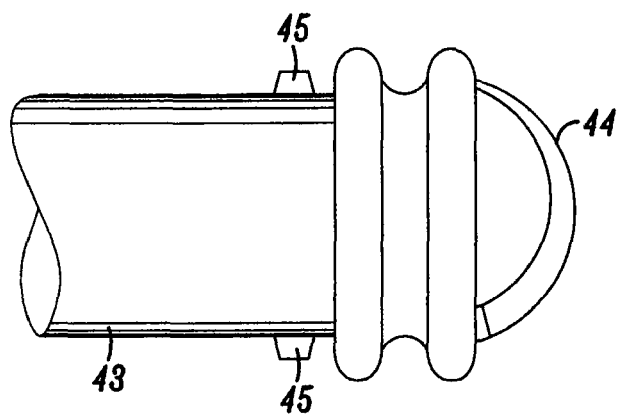

With reference first to FIGS. 1 to 3, the tracheostomy tube assembly comprises an outer tracheostomy tube 1 and a removable inner cannula 20 inserted within the outer tube. The outer tube 1 has a shaft 10 with an inflatable sealing cuff 11 that embraces the forward section 11 close to the patient end 12 of the tube, the cuff being inflated via an inflation lumen 13 and a combined connector and inflation indicator 14. At its rear or machine end 15 the outer tube 1 has a hub 16 and flange 17 to which a retaining tape (not shown) can be fastened for securing the tube with the patient's neck. The outer tube 1 could have an internal diameter between about 2 mm and 10 mm, and its length could be between 60 mm and 200 mm.

The inner cannula 20 includes a shaft 21 of circular section having at its rear or machine end an end fitting or machine end region 22. The shaft 21 is of a thin, stiff plastics material, such as PVC, polyurethane, polyethylene, polypropylene, PTFE or other flexible or semi-rigid plastics material. The external diameter of the shaft 21 is selected to be just smaller than the inner diameter of the shaft 10 of the outer tube so that the inner cannula can be readily inserted and removed from the outer tube. The machine end region or fitting 22 is shaped to locate within the hub 16 of the tracheostomy tube 1 and prevent the inner cannula 20 extending beyond the patient end 12 of the tube. The end fitting 22 is also arranged to be retained securely within the hub 16 until it needs to be removed. This is achieved by means of several surface formations in the form of catches 23 projecting outwardly around the outside of the end fitting 22. The catches 23 are positioned to lie on the patient side of a surface formation 24 formed around the inside of the hub 16. The surface formation 24 on the hub 16 takes the form of a continuous rib or step around the inside of the hub. The rib 24 and catches 23 are preferably shaped in a manner that allows the catches to slide over the rib during insertion of the inner cannula 20 more readily than they can slide over the rib when an axial force is applied to the inner cannula to pull it out of the tracheostomy tube 1. The end fitting 22 is, however, shaped such that the catches 23 are displaced radially inwardly when an angular, twisting force is applied to the machine end of the end fitting. More particularly, the major part of the length of the end fitting 22 is formed by a series of twelve parallel, longitudinally-extending thin struts 26 extending between a forward, patient end collar 27 and a rear, outer or machine end collar 28. The struts 26 are laterally spaced from one another and each have a shallow bend in the cylindrical plane along which the struts lie, giving them a slight S or dog-leg shape to enable then to bend more easily. The catches 23 are formed on the outside of each strut 26 spaced a short distance from their machine end. The machine end collar 28 is formed with V-shape longitudinal grooves 29 on its inner surface between each strut 26 extending to a depth of about half the thickness of the collar. These grooves 29 enable the collar to buckle inwardly more easily when twisted. The end fitting 22 also includes a grip 30 by which the machine end of the end fitting can be gripped to enable the inner cannula 20 to be removed from the tracheostomy tube 1. The grip 30 takes the form of two semi-circular rings 31 hingedly mounted with the machine end collar 28 by two opposite links 32. The rings 31 normally lie flat in a radial plane as shown in FIG. 2 and project a short distance beyond the machine end of the hub 16 so that they can be gripped between finger and thumb. When gripped, the two rings 31 fold up towards one another to provide a stable grip structure 30 extending laterally of the end fitting 22. The grip 30 enables the machine end collar 28 to which it is attached to be twisted about the axis of the end fitting 22. This causes the struts 26 to flex both rotationally and inwardly, thereby causing the catches 23 to be moved radially inwardly and out of contact with the rib 24 around the inside of the hub 16.

The arrangement described above enables a twisting movement of an outer end of the machine end region or fitting 22 about the axis of the inner cannula 20 to displace the surface formations 23 on the inner cannula away from the engagement formation 24 on the hub 16 sufficiently to allow the inner cannula to be pulled rearwardly out of the tracheostomy tube 1 by collapsing the end fitting inwardly away from contact with the hub. There are, however, other arrangements by which a twisting movement can be used to release engagement of the inner cannula with the hub of a tracheostomy tube, such as shown in FIGS. 4 to 7. In this arrangement, the hub 40 of a tracheostomy tube 41 is formed with two inwardly-projecting surface formations in the form of lugs 42 arranged diametrically opposite each other. The inner cannula 43 is formed at its machine end with the same kind of grip arrangement 44 as shown in FIG. 2 and, just forwardly, to the patient side, of this the cannula has two outwardly-projecting catches 45 positioned to lie just forwardly to the two lugs 42 when the cannula is fully inserted in the tracheostomy tube 41. The machine end of the inner cannula 43 in this arrangement is not collapsible as in the previously-described arrangement but is relatively rigid radially. The inner cannula 43 is inserted in the tracheostomy tube 41 by orienting it so that the catches 45 are out of alignment with the lugs 42 in the hub 40, thereby enabling the inner cannula to be fully inserted in the tube. The inner cannula 43 is then locked in place simply by gripping the grip 44 and twisting the end of the cannula to displace the catches 45 into position forwardly of the lugs 42. To remove the inner cannula 43 the grip 44 is simply twisted to angularly displace the machine end through a small angle to displace the catches 45 away from the lugs 42 and thereby enable the cannula to be pulled out. In this arrangement the entire shaft of the cannula 43 must be sufficiently flexible about its axis to enable it to be twisted in the tracheostomy tube 41. The need for the shaft to be flexible reduces the choice of materials that can be used for the shaft. The arrangement also relies on the user twisting the cannula 43 after insertion to lock it securely in position whereas the previously-described arrangement simply has to be released to lock the cannula in place.

Figure 8:
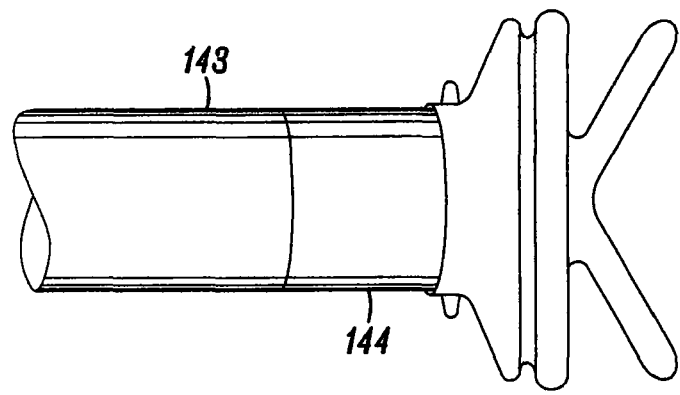
FIG. 8 is a side elevation view of a third form of alternative inner cannula.
Figure 9:
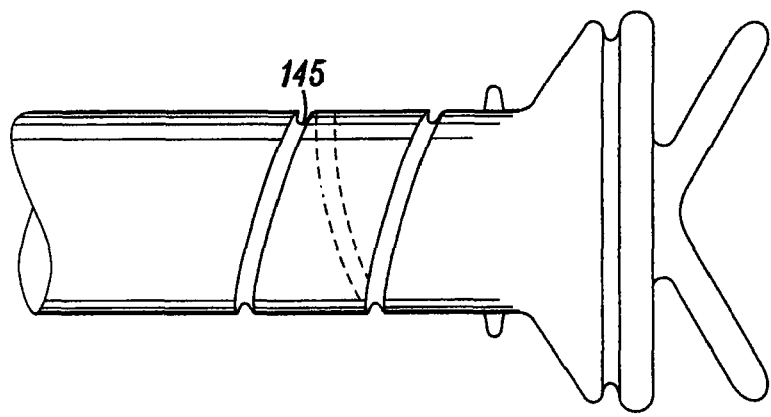
FIG. 9 is a side elevation view of a fourth form of alternative inner cannula.

In order to overcome the need for the entire inner cannula shaft to be flexible, an alternative arrangement as shown in FIG. 8 could be provided. This inner cannula 143 is very similar to that shown in FIGS. 6 and 7 except for the inclusion of a short section 144 of the shaft adjacent the machine end formed of a different, more flexible material, such as a thermoplastic elastomer (TPE). In this arrangement the section 144 can be twisted relatively easily for locking and unlocking, without the need to twist the entire shaft. In another alternative arrangement shown in FIG. 9 the shaft is made entirely of the same material but has a short section adjacent the machine end with a helical groove 145 formed through the thickness of the wall of the cannula (that is, creating a raised helical rib on the inside of the cannula) that enables the machine end of the grooved section to be twisted slightly relative to its patient end.

Figure 10:
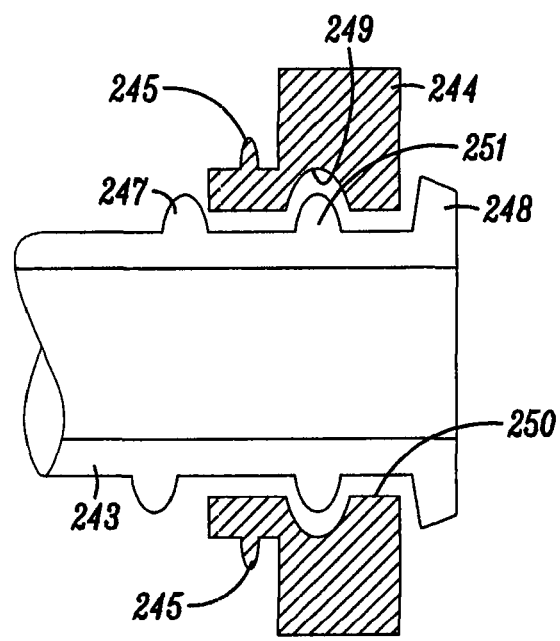
FIG. 10 is a cross-sectional side elevation view of the machine end of a fifth form of alternative inner cannula.
Figure 11:
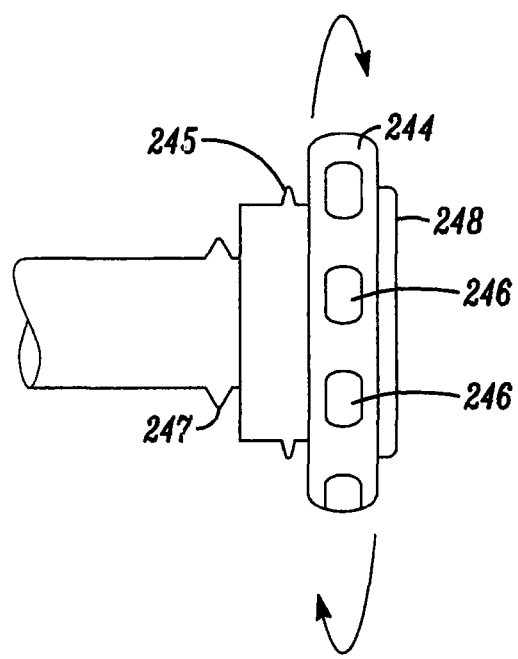
FIG. 11 is a side elevation view of the fifth form of inner cannula.

A further alternative arrangement by which twisting of the cannula can be avoided is shown in FIGS. 10 and 11. In this arrangement, the inner cannula 243 has a separate, rotatable component 244 at its machine end on which the locking formations 245 are formed so that only this part of the cannula needs to be twisted for locking and unlocking. This rotatable component 244 takes the form of a circular ring having knurls 246 or the like around its outer edge to improve grip. The ring 244 is trapped between two outwardly projecting annular ribs 247 and 248 on the inner cannula 243. The rotatable ring 244 also has an annular channel 249 midway along its bore 250, which locates over a third, central rib 251 on the inner cannula. The rotatable ring 244 could be a separately formed component subsequently assembled on the machine end of the inner cannula 243. Alternatively, it could be made by an over-moulding process in which the inner cannula is moulded in one cavity and then transferred to a second cavity where the locking ring is over-moulded in a second, different, incompatible material selected such that the shrinkage of the two materials is sufficient to ensure that the two parts do not bond together but enable them to be rotated relative to one another.

The invention claimed is:

1. An inner cannula for a tracheostomy tube, the inner cannula including a tubular shaft and a machine end region arranged to fit within a hub at a machine end of the tracheostomy tube, characterised in that an outer surface of the machine end region of the inner cannula and an inner surface of the hub on the tracheostomy tube are provided with cooperating engagement formations arranged to retain the inner cannula in the hub of the tracheostomy tube against an axial force tending to withdraw the inner cannula from the tracheostomy tube, and that the machine end region is arranged such that twisting an outer end of the machine end region about an axis of the inner cannula displaces the engagement formation on the inner cannula away from the engagement formation on the hub sufficiently to allow the inner cannula to be pulled rearwardly out of the tracheostomy tube, wherein the outer end of the machine end region is connected with a forward end of the machine end region by a collapsible region, and that the engagement formation on the machine end region is provided on the collapsible region such that twisting the outer end of the machine end region relative to the forward end causes the collapsible region to collapse inwardly and displace the engagement formation on the machine end region inwardly out of engagement with the engagement formation on the hub.

2. An inner cannula according to claim 1, characterised in that the collapsible region is provided by a plurality of struts extending generally parallel to one another and extending generally longitudinally of the machine end region.

3. An inner cannula according to claim 2, characterised in that the struts are curved or bent along their length.

4. An inner cannula according to claim 2, characterised in that the struts extend forwardly from a circular machine end collar, and that the collar is formed with a plurality of grooves around its inner surface to enable the collar to buckle when twisted.

5. An inner cannula according to claim 1, characterised in that the inner cannula includes a machine end grip having two hinged rings mounted with the machine end region of the inner cannula such that the rings can be folded together and gripped to enable the machine end region of the inner cannula to be twisted and pulled rearwardly.

6. An inner cannula according to claim 1, characterised in that the hub has a circumference and that the engagement formation on the hub extends around only a part of the circumference of the hub and the engagement formation on the machine end region of the inner cannula such that the engagement formations on the hub and the machine end region can be displaced out of engagement by twisting the machine end region relative to the hub to enable the inner cannula to be removed from the tracheostomy tube.

7. An inner cannula according to claim 6, characterised in that the inner cannula has at least a part of its length that is flexible about the axis of the inner cannula such that the machine end region of the inner cannula can be angularly displaced relative to a patient end of the inner cannula.

8. An inner cannula according to claim 6, characterised in that the inner cannula has a separate rotatable component, and that the engagement formation on the inner cannula includes engagement formations provided on the rotatable component.

9. A tracheostomy tube assembly including a tracheostomy tube and an inner cannula fitted in the tracheostomy tube, wherein the inner cannula includes a tubular shaft and a machine end region fitted within a hub at a machine end of the tracheostomy tube, characterised in that an outer surface of the machine end region of the inner cannula and an inner surface of the hub on the tracheostomy tube are provided with cooperating engagement formations arranged to retain the inner cannula in the hub of the tracheostomy tube against an axial force tending to withdraw the inner cannula from the tracheostomy tube, and that the machine end region is arranged such that twisting an outer end of the machine end region about an axis of the inner cannula displaces the engagement formation on the inner cannula away from the engagement formation on the hub sufficiently to allow the inner cannula to be pulled rearwardly out of the tracheostomy tube, wherein the outer end of the machine end region is connected with a forward end of the machine end region by a collapsible region, and that the engagement formation on the machine end region is provided on the collapsible region such that twisting the outer end of the machine end region relative to the forward end causes the collapsible region to collapse inwardly and displace the engagement formation on the machine end region inwardly out of engagement with the engagement formation on the hub.

* * * * *